(12) United States Patent
Karthikeyan et al.

(10) Patent No.: US 11,456,061 B2
(45) Date of Patent: Sep. 27, 2022

(54) METHOD FOR HARVESTING 3D CHEMICAL STRUCTURES FROM FILE FORMATS

(71) Applicant: Council of Scientific & Industrial Research, New Delhi (IN)

(72) Inventors: Muthukumarasamy Karthikeyan, Pune (IN); Renu Vyas, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 1101 days.

(21) Appl. No.: 16/072,097

(22) PCT Filed: Jan. 19, 2017

(86) PCT No.: PCT/IN2017/050029
§ 371 (c)(1),
(2) Date: Jul. 23, 2018

(87) PCT Pub. No.: WO2017/125950
PCT Pub. Date: Jul. 27, 2017

(65) Prior Publication Data
US 2021/0210173 A1    Jul. 8, 2021

(30) Foreign Application Priority Data
Jan. 22, 2016   (IN) .............................. 201611002390

(51) Int. Cl.
| G16C 20/80 | (2019.01) |
| G16C 20/40 | (2019.01) |
| G16C 20/70 | (2019.01) |

(52) U.S. Cl.
CPC ............. *G16C 20/80* (2019.02); *G16C 20/40* (2019.02); *G16C 20/70* (2019.02)

(58) Field of Classification Search
CPC ......... G16C 20/40; G16C 20/60; G16C 20/80
See application file for complete search history.

(56) References Cited

U.S. PATENT DOCUMENTS 5,157,736 A    10/1992  Byer et al.
6,073,080 A *   6/2000  Tomonaga ............ G06T 11/206
                                                      702/22
(Continued)

FOREIGN PATENT DOCUMENTS

| WO | WO2013030850 A2 | 3/2013 |
| WO | WO2013163068 A1 | 10/2013 |

OTHER PUBLICATIONS

Bayati, Parallel Methods for Protein Coordinate Conversion, Published by ProQuest LLC (Year: 2015).*

(Continued)

*Primary Examiner* — Michael J Dalbo
(74) *Attorney, Agent, or Firm* — Dinsmore & Shohl, LLP (57) ABSTRACT

A method and system for harvesting molecular structures from non-editable documents is disclosed herein. A non-editable storage document is fed by a feeder which is received by a receiver. The molecular and non-molecular data contained in the non-editable storage document is recognized. The three-dimensional coordinates of the molecular data is separated using a pattern recognition. The molecular coordinates are encoded by a pattern sequence. A bond matrix data of the encoded data is generated. Subsequently the bond matrix data for accuracy is verified by comparing with a stored standardized data into a library.

8 Claims, 9 Drawing Sheets

(56) References Cited

U.S. PATENT DOCUMENTS

| | | | | |
|---|---|---|---|---|
| 2003/0002067 A1* | 1/2003 | Miyano | ................. | B41J 11/663 |
| | | | | 358/1.14 |
| 2011/0276589 A1* | 11/2011 | Smith | ................. | G06V 30/422 |
| | | | | 707/769 |
| 2013/0174017 A1 | 7/2013 | Richardson et al. | | |
| 2014/0301608 A1* | 10/2014 | Karthikeyan | ......... | G16C 20/80 |
| | | | | 382/113 |

OTHER PUBLICATIONS

Sadowski, From Atoms and Bonds to Three-Dimensional Atomic Coordinates: Automatic Model Builders, Chem. Rev. 1993, 93, 2567-2581 (Year: 1993).*

Jessop et al., "Mining chemical information from open patents", Journal of Cheminformatics, 3:40, 2011, pp. 1-17.

Filippov et al., "Optical Structure Recognition Software to Recover Chemical Information: OSRA, An Open Source Solution", Journal of Chemical Information and Modeling, vol. 49, 2009, pp. 740-743.

Sadowski et al., "From Atoms and Bonds to Three-Dimensional Atomic Coordinates: Automatic Model Builders", Chemical Reviews, American Chemical Society, vol. 93, 1993, pp. 2567-2581.

International Search Report and Written Opinion completed Jul. 5, 2017, pertaining to PCT/IN2017/050029 filed Jan. 19, 2017.

International Preliminary Report on Patentability dated Jul. 24, 2018, pertaining to PCT/IN2017/050029 filed Jan. 19, 2017.

* cited by examiner

| Symbol | NA | NB | NC | Bond* |
|---|---|---|---|---|
| C | | | | |
| S | 1 | | | 1.8306635 |
| C | 2 | 1 | | 1.8306635 |
| H | 1 | 2 | 3 | 1.0947890 |
| H | 1 | 2 | 3 | 1.0940765 |
| H | 1 | 2 | 3 | 1.0940765 |
| H | 3 | 2 | 1 | 1.0947890 |
| H | 3 | 2 | 1 | 1.0940765 |
| H | 3 | 2 | 1 | 1.0940765 |
| ? | 2 | 1 | 3 | 0.5786000 |

METHOD FOR HARVESTING 3D CHEMICAL STRUCTURES FROM FILE FORMATS

FIELD OF INVENTION

The present invention relates to a method for harvesting a molecular data from the supporting information contained in the document format. More particularly, the present invention relates to a method and system that enables large scale conversion of molecular information from supplementary data available in the non-readable document into a collection of ready-to-compute molecular data to create an automated workflow for advanced computational processes.

BACKGROUND & PRIOR ART

Harvesting chemical data from the web is a challenging task requiring several convoluted steps. chemical names (common, systematic). Chemical Abstract Registry numbers are extracted from the web-pages and transformed into corresponding molecular structures using name-to-structure conversion tools, name to structure relational database look-up methods, large scale key-value pair list, distributed relational database search etc. Transforming the raster images into vector graphics followed by identification of relevant pixel information associated with atoms and bonds of a molecule is a cumbersome job. Tools have also been developed to harvest molecular data from images using web camera, scanned images wherein the raster graphics data was transformed into vector graphics to eventually retrieve the atoms and bonds information for the generation of truly computable and re-usable chemical structures such as ChemRobot, OSRA, ChemReader, CLiDE, but only limited success has been achieved.

When chemical structures are stored in truly computable format with atoms and bond matrices (vector format-Cartesian co-ordinates), they can be processed electronically for computational and informatics purposes. However while transforming/storing the files in PDF (Printable/Portable Document/Data Format) that are usually used for the convenience of printing and reading, the valuable and re-usable molecular data is totally lost and buried in scientific literature as documents and seldom used for further computational studies. In earlier days, the hand-drawn molecules in ORTEP diagram formats were published while discussing the 3D conformation of molecules in the research articles. Generation of 3D structures from these molecular images in raster format was extremely difficult. Recently, some efforts have been made to transform computer generated and hand-drawn chemical images from journal articles and patent documents into truly computable molecules for inventory and database applications. Other similar endeavors include transforming either the textual chemical names (common, systematic, corporate identifiers for example CAS Registry number) or the computer generated names into corresponding molecular structures with moderate success. A foolproof method with complete reproducibility of computable molecules from images is still a distant dream as the existing methodologies and tools do not provide accurate molecule data after processing. Therefore it is essential to develop efficient tools that can extract molecules from rich sources such as supplementary information files deposited at the journal site. Although spectral, molecular and analytical data have been harvested in the past but extracting molecules directly from author supplied atomic coordinates provided in supplementary materials as PDF format is not known.

U.S. Pat. No. 6,073,080 discloses a computer system in which molecular structural diagram is produced. The computer system has storage means for storing the bonding atom pair data. The bonding atom pair data is extracted. Each atom of the compound extracted is classified into either of a cyclic portion and a chain portion. Two-dimensional coordinates of each atom classified are obtained. Based on the two-dimensional coordinates, a molecular structural diagram is produced.

The Earlier published application WO2013030850 of the present inventor discloses a method of extracting and then reusing/remodeling chemical data from a hand written or digital input image without manual inputs. The method converts the input image into a greyscale image and then again into a binary image. It proceeds to identify the circle bond inside the ring of the input image and the double bond and triple bond. The method further identifies the zones containing text in the input image. The output is generated as a molecular structure of the input image.

A tool named "Structure Clipper", as published in Pfizer bulletin, performs automated extraction of chemical structures from a native PDF document. The extracted structures are traceable to the document page and source location. However, the image to structure conversion is performed using the standard OSRA and OCR techniques.

A product named Document to Structure (D2S), powered by ChemAxon's Naming technology processes PDF, HTML, XML, text files and office file formats: DOC, DOCX, PPT, PPTX, XLS, XLSX, ODT. It recognizes and converts the chemical names (IUPAC. CAS, common and drug names). SMILES and InChI found in the document into chemical structures.

An article titled "Mining chemical information from Open patents" by David M. Jessop et. al. published in *Journal of Cheminformatics* 2011 discusses PatentEye, a prototype system for the extraction and semantification of chemical reactions from the patent literature.

WO2013163068 discloses a method and apparatus for performing an accurate search of chemical or molecular compounds to enhance the drug discovery process. FIG. 2 of WO'068 demonstrates that the data being extracted from is a PDF file.

Although the name to chemical structure conversion methods are now routinely being used for harvesting chemical data from documents, such methods have been insufficient in generating the accurate and truly computable and re-usable molecular data. The supporting information related to computational methods based research articles describing the transition states of organic reactions is now available from journal publishers' websites containing description of computations performed with tables of results, molecular images in 3D conformations along with the molecular co-ordinates in a PDF format. This combined data in a single file complicates the harvesting process and development of pattern recognition techniques for selectively excluding the non-atomic co-ordinate information from the pool of large collection of textual data presented as supporting material. Since there are no defined rules and guidelines for submitting molecular data in a supporting document associated with research publications, the authors are free to choose their favorite methods of representing molecular data such as chemical structures and corresponding atomic co-ordinates in the supplementary data file. This freedom of choosing data formats necessitates the development of several pattern recognition templates in the form of regular expressions to handle diverse formats (co-ordinates separated by space, comma, tab etc.) and maintain the order in which the XYZ co-ordinates and atom information is presented by the authors.

Further, several standard molecular representations in ASCII format are available, which are easily readable by molecular modeling and chemoinformatics software packages. Supporting materials are deposited in PDF format for the convenience of storage, easy manageability and electronic dissemination. The commercial software packages applied for computational chemistry applications employ their own legacy file formats for handling molecular data, however the technical details are not usually published. From the researchers' point of view, the published data in re-usable formats would save efforts and time to understand the molecular data better and use it for practicing to carry out further advanced studies in different problem solving environments that require 3D conformation of molecules. Exchange of chemical data between multiple softwares without loss of information is a critical requirement in computational chemistry and chemoinformatics applications.

Thus there is a need for the development of tools that can bridge the gap in molecular data translation automatically and accurately from PDF format to truly computable, re-usable format without manual intervention.

OBJECTS OF THE INVENTION

It is an object of the present invention to extract molecular data stored in complex non-readable documents of supplementary materials deposited along with scientific research articles.

Another object of the invention is to provide ready to compute molecules by generating a coordinate matrix of given cluster of atoms. It is derived from the XYZ co-ordinates of 3D co-ordinate data recognized by pattern matching that was used to generate SDF/MOL formats for the creation of 3D molecules.

Yet another object of the invention is to provide a large scale conversion of molecular information from supplementary documents available in the PDF format into a collection of ready-to-compute molecular data to create an automated workflow for advanced computational processes.

SUMMARY OF THE INVENTION

Accordingly, the present invention discloses a method for harvesting three-dimensional chemical data from a storage document and converting into recognizable data. A non-editable storage document is fed by a feeder which is received by a receiver. The molecular and non-molecular data contained in the non-editable storage document is recognized. The three-dimensional coordinates of the molecular data is separated using a pattern recognition. The molecular coordinates are encoded by a pattern sequence. A bond matrix data of the encoded data is generated. Subsequently the bond matrix data for accuracy is verified by comparing with a stored standardised data into a library.

In another embodiment, a system for harvesting three-dimensional chemical data from a storage document and converting into recognizable data is disclosed. It comprises a feeder to feed a non-editable storage document, a receiver to receive a non-editable storage document, a library having standardized data stored, and an analyser.

The analyser:
recognizes molecular and non-molecular data contained in said non-editable storage document,
separates three-dimensional coordinates of said molecular data using a pattern recognition.
encodes molecular coordinates by a pattern sequence,
generates a bond matrix data of said encoded data, ensuring reusability of the data,
verifying said bond matrix data for accuracy by comparing with a stored standardised data into said library.

In an aspect of the invention, the molecules are converted from a non-editable storage document such as pdf format to standard interoperability formats such as sdf and gjf.

In yet another aspect of the invention, molecular block may be identified from the coordinates to avoid complications due to pagination of the document.

DETAILED DESCRIPTION OF THE INVENTION

The invention will now be described in detail in connection with certain preferred and optional embodiments, so that various aspects thereof may be more fully understood and appreciated.

Figure 1:
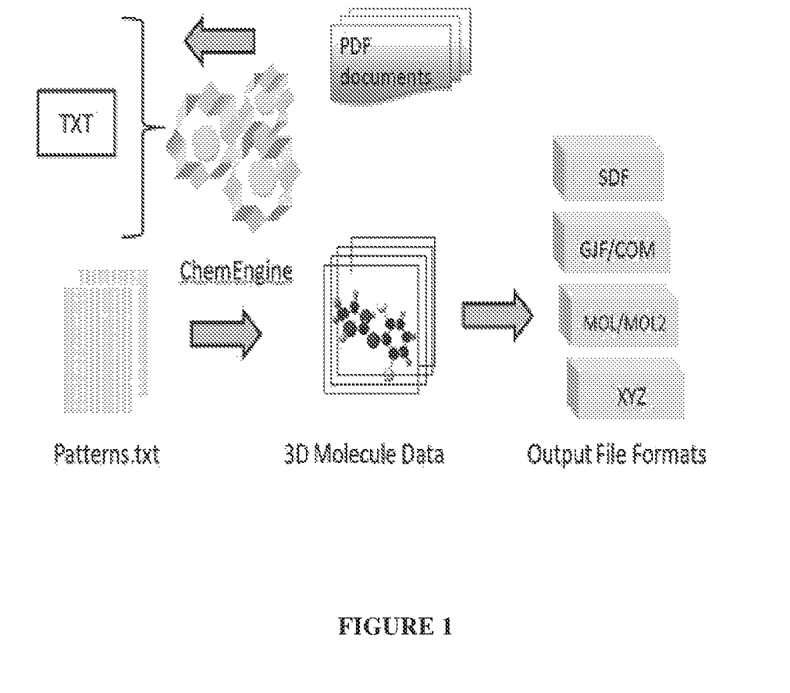
FIG. 1 is a schematic representation of the inventive concept described in the present invention.

FIG. 1 provides a schematic representation of the method of the present invention. An electronic image document or a non-editable document such as pdf files is provided as an input. The said document also contain a brief description of molecules, computed data, plots, page numbers, document information, manuscript bibliographic details etc. as a single document. Harvesting the molecular data from such electronic document is difficult as the data have to be excluded while parsing the electronic document. The method of the present invention recognizes the molecular data from the coordinates in text format and separates it from the remaining relevant but non-molecular text.

Figure 2:
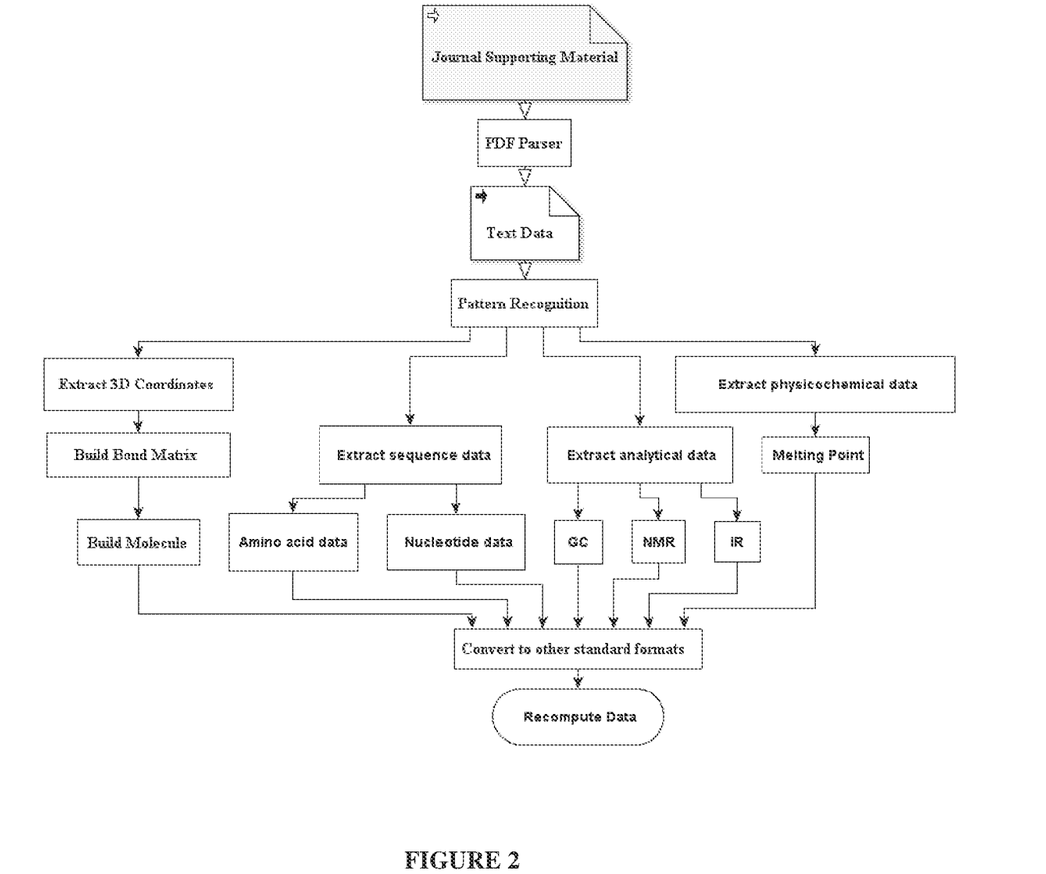
FIG. 2 illustrates the computational steps workflow for extracting re-computable molecular structures from PDF articles as implemented in in the present invention

FIG. 2 illustrates the complete steps employed, which include step of the present invention. Firstly, the data in the non-editable document such as PDF file is converted into textual data using a simple PDF parser. The textual data retrieved is then analyzed using a pattern recognition method to separate the 3D coordinates from the non-molecular text for the identification of atomic co-ordinates and atom information. All the X,Y,Z coordinates are encoded by a general pattern sequence consisting of 2 characters, followed by a space, an addition or subtraction symbol, a number, decimal and eight digits succeeding the decimal.

Figure 3:
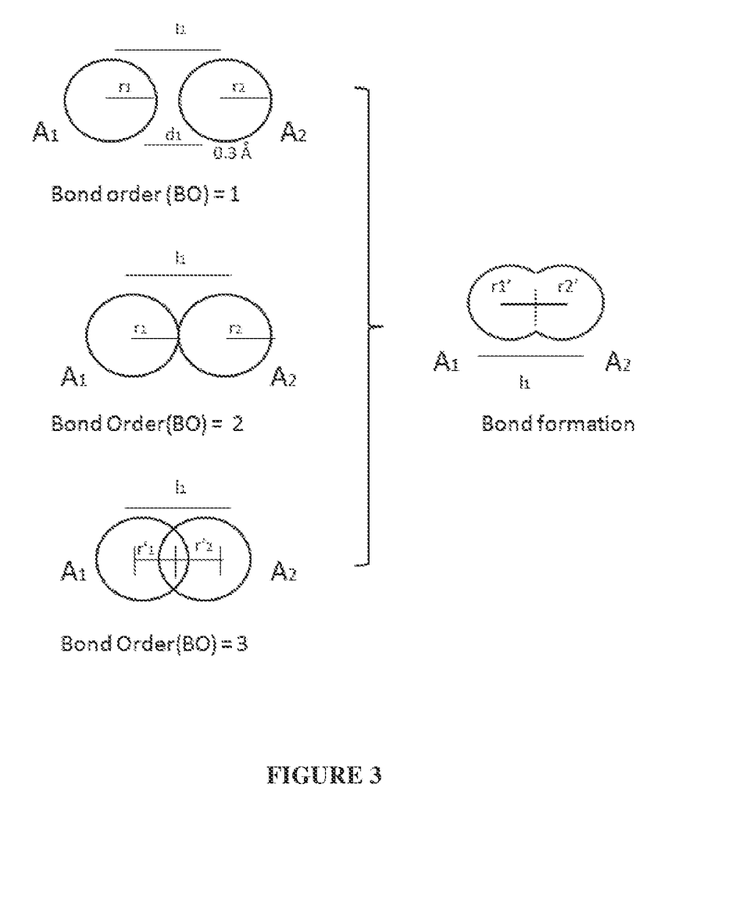
FIG. 3 illustrates the logic implemented in the present invention for bond matrix creation.
Figure 4:
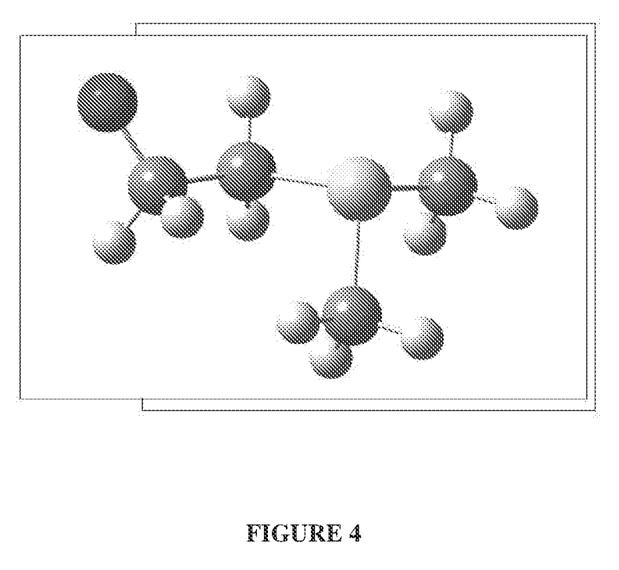
FIG. 4 illustrates the illustrates the standardized (optimized geometries conformation) of a torsional rotational transition state reproduced using the method of the present invention by harvesting the 3D coordinate structural data from the textual patterns generated for the pdf file containing the supporting material.

Once the coordinate file is created, the bond matrix is computed to provide the interconnectivity information for reconstructing the original molecules reported in the supplementary material of the research article. The computation of the bond matrix is illustrated in FIG. 3. Important parameters such as bond angles, bond lengths and dihedral angles are verified and checked for consistency in the recreated molecule and then saved in the original file format, for instance gjf. The coordinate data and bond matrix information is used to create molecules in standard interoperability formats such as .sdf or .mol as ready to compute molecules for the convenience of the user. This process avoids unnecessary generation of molecular data and laborious recomputation of already published work. The molecules can be subjected to further simulations such as descriptor calculation, energy profile, docking etc.

A method of the present invention facilitates the generation of a bond matrix from the coordinate atom type information. The interatomic distances of all the elements in the periodic table are taken into account to annotate the bond order between two atoms. The cut off distance between two vicinal atoms involved in a covalent bond formation was calculated as the sum of atomic radii+a scaling factor of 0.35 Å, any distance higher than this was considered as a non-bonding interaction by the program. Likewise all interatomic distance of other atoms were computed to generate bond matrix of a molecule.

In another aspect of the invention, the molecules are converted from doc or txt document format.

The following examples, which include preferred embodiments, will serve to illustrate the practice of this invention, it being understood that the particulars shown are by way of example and for purpose of illustrative discussion of preferred embodiments of the invention.

Example 1

Figure 5:
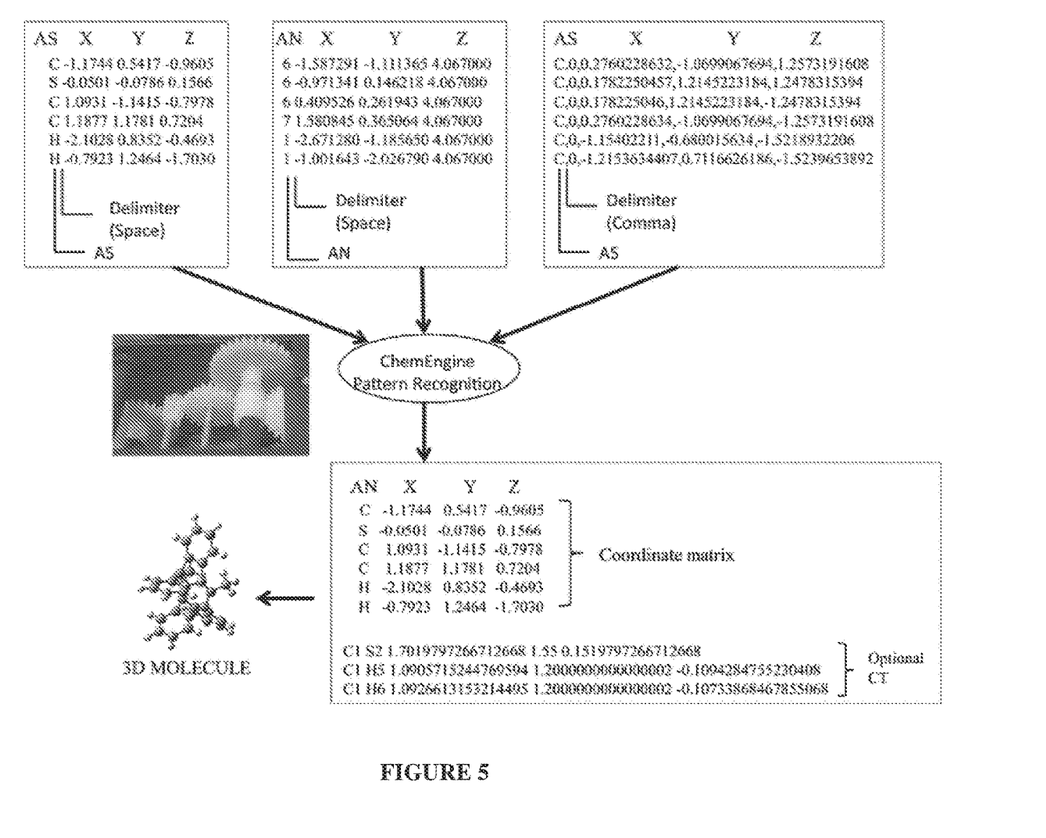
FIG. 5 highlighting the challenges posed by the diverse coordinate formats present in the supplementary table of journal articles.

A supporting material file relating to a reaction modeling research paper describing the mechanistic investigation of epoxide formation from sulfur ylides and aldehydes was considered. The PDF file was processed to directly extract a .txt file from which patterns were discerned to generate the coordinates data. An important constraint for generating ready to compute molecules was the non-availability of bond order information in the published coordinates data. In view of the aforesaid problem, the method of the present invention has been provided with creation of bond matrix, that is inter-atomic connectivity of a given cluster of atoms. The method accurately retained the original conformations of all the optimized molecules when the extracted atomic coordinates were supplied back to the original program, which is illustrated in FIG. 5.

To validate the accuracy of the proposed method, the bond matrix for atoms of all the molecules (n=29) deposited in the research article was computed and compared with the ones generated by the original software called as Gaussian. The values were identical in both the cases. The coordinate data and the computed connectivity information, that is bond matrix, could be used to generate molecules in the SDF and MOL formats. The bond matrix output generated by the present invention for the first molecule is given below.

Mol_1    1    C1    S2    1.7019797266712668    1.55    0.1519797266712668
Mol_1    2    C1    H5    1.0905715244769594    1.2000000000000002    −0.1094284755230408
Mol_1    3    C1    H6    1.0926613153214495    1.2000000000000002    −0.10733868467855068
Mol_1    4    S2    C3    1.829628926859214    1.55    0.279628926685921403
Mol_1    5    S2    C4    1.851840751792659    1.55    0.3018407517926589
Mol_1    6    C3    H7    1.095048094834195    1.2000000000000002    −0.10495190516580521
Mol_1    7    C3    H8    1.0929989249765986    1.2000000000000002    −0.10700107502340162
Mol_1    8    C3    H9    1.09433679459296227    1.2000000000000002    −0.10566320540703744
Mol_1    9    C4    H10    1.0946906229615743    1.2000000000000002    −0.10530937703842591
Mol_1    10    C4    H11    1.0934381646897096    1.2000000000000002    −0.10656183531029062
Mol_1    11    C4    H12    1.0947090115642606    1.2000000000000002    −0.10529098843573959

To understand the atomic (electronic) movements and distances, which is of paramount importance in transition state modeling studies of organic reactions, typically the cut-off distance for the presence of a bond is computed as the sum of the covalent radii of the two atoms.

Figure 6:
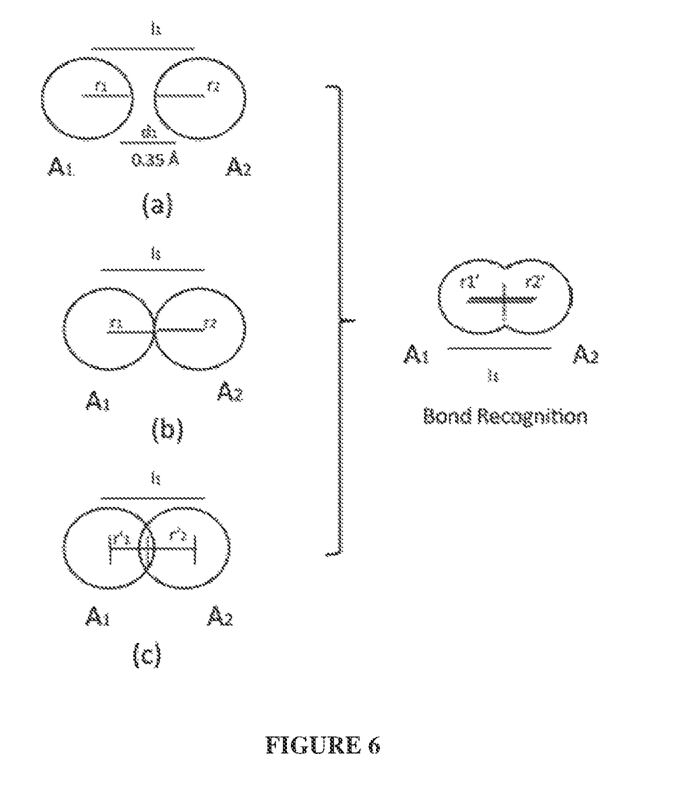
FIG. 6 depicts the bond recognition process implemented in the present invention. a, b, c represent three scenarios between two interacting atoms A1 and A2, wherein a bond was considered to be present.

For the same purpose, the interatomic distances of all the elements in periodic table are taken into account to annotate the bond order between two atoms. The creation of a bond matrix between two atoms A1 and A2 in a molecule according to the present invention, is schematically represented in FIG. 6. The cut off distance between two vicinal atoms involved in a covalent bond formation was calculated as the sum of atomic radii+a scaling factor of 0.35 Å, any distance higher than this was considered as a non-bonding interaction by the program. Likewise all interatomic distance of other atoms were computed to generate bond matrix of a molecule.

Figure 7:
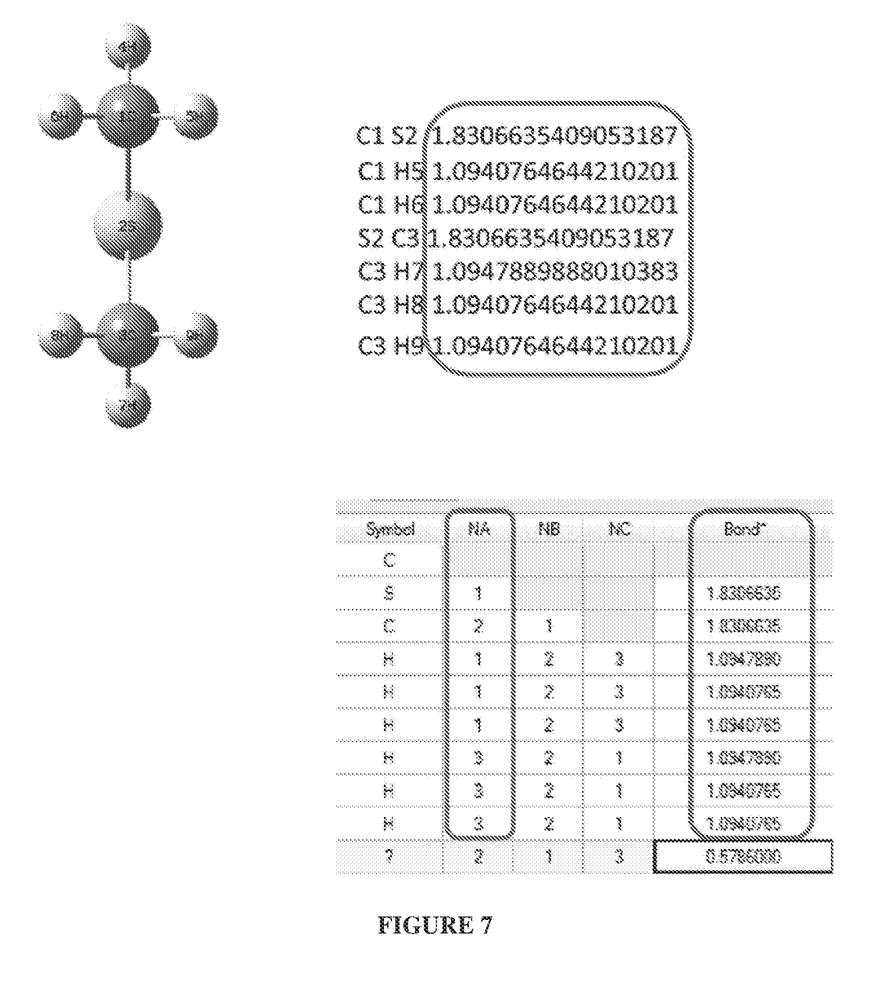
FIG. 7 illustrates interatomic bond distances of Dimethyl sulfide (Mol ID 29) reproduced using the method of the present invention.

To validate method of the present invention, the bond matrix for atoms of all the molecules (n=29) deposited in the supplementary information of the research article was computed and compared with the ones generated by the original software (Gaussian). The values were identical in both the cases. Bond matrix conformation of a representative molecule from this set is shown in FIG. 7. The coordinate data and the computed connectivity information could be used to generate molecules in the SDF and MOL formats.

Example 2

The input is a well cited paper wherein computational studies were performed on a range of alkenes to gain insights into the mechanistic processes involved in the thiolene reactions typically classified under click chemistry. In contrast with the demonstration in Example 1, where the approach was straight forward and an open source pdf reader was employed to convert pdf to text from the supporting information submitted in a pdf file, in the present case the pdf file was first saved in a plain text format externally and then fed as an input to the method of the present invention for extracting the coordinates. The inadvertent errors in file conversion are related to compatibility issues associated with various PDF maker programs available on the web. The method of the present invention successfully generated the Cartesian coordinates, bond matrix and non-molecular data of all the reported molecules. Due to the pagination problem in the original PDF document, only few structures partially failed. That is to say, few atoms carry forward to next molecule. This pagination issue was later addressed by molecular block identifier.

MOL_0
C −0.04781100 1.16216400 0.00000000
H −1.09556300 1.46309200 0.00000000
H 0.43082600 1.55738100 0.89506100
H 0.43082600 1.55738100 −0.89506100
S −0.04781100 −0.66970400 0.00000000
H 1.28575000 −0.83557700 0.00000000
MOL_1
C −1.11122700 0.00005600 −0.00880200
H −1.42403800 −0.00270000 1.04234300
H −1.51094200 0.90050300 −0.47689500
H −1.51064400 −0.89830400 −0.48120000
S 0.69456200 0.00001000 −0.00196500
MOL_2
C −1.28038600 0.22044600 −0.00000100
H −1.30140400 1.30644800 −0.00003900
H −2.23896200 −0.28606800 0.00010900
C −0.13464400 −0.45374900 −0.00003700
H −0.16675400 −1.54212600 0.00001400
C 1.23345600 0.16237100 0.00000400
H 1.80706400 −0.15250500 0.87891300
H 1.80774100 −0.15382800 −0.87798100
H 1.18176300 1.25366800 −0.00081300

Table 1 summaries of the results of the examples representing the diversity of coordinate molecular data in supplementary material handled by the present invention.

| Entry | Case Study | N = molecules | Regular Expression pattern | Format & Delimiter |
|---|---|---|---|---|
| 1 | Epoxide formation from sulfur ylides and aldehydes | 29 | ^[A-Za-z0-9]{1, 2}\\s+−{0, 1}.{1, 2}[0-9]{1, 8}\\s+−{0, 1}.{1, 2}[0-9]{1, 8}.{1,} | PDF Space |
| 2 | Thiolene click chemistry | 115 | ^[A-Za-z0-9]{1, 2}\\s+−{0, 1}.{1, 2}[0-9]{1, 8}\\s+−{0, 1}.{1, 2}[0-9]{1, 8}.{1,} | Text Space |
| 3 | Design of tetra(arenediyl)bid(allyl) derivatives for cope rearrangement transition states | 55 | ^[A-Za-z0-9]{1, 2}\\,[0]{0, 1}[\\,]{0, 1}−{0, 1}.{1, 2}[0-9]{1, 10}\\,−{0, 1}.{1, 2}[0-9]{1, 10}.{1,} | PDF Comma. |

Figure 8:
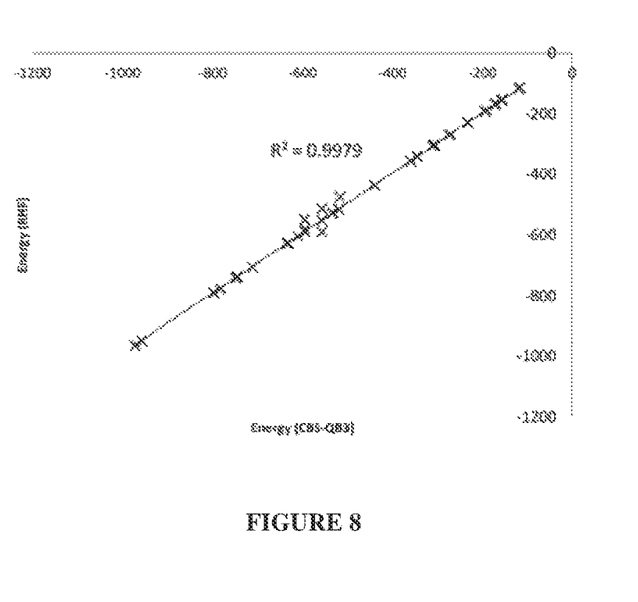
FIG. 8 illustrates a comparative plot of single point energies of molecules extracted from coordinate data of Example 2. The values are in agreement with the original computed data.
Figure 9:
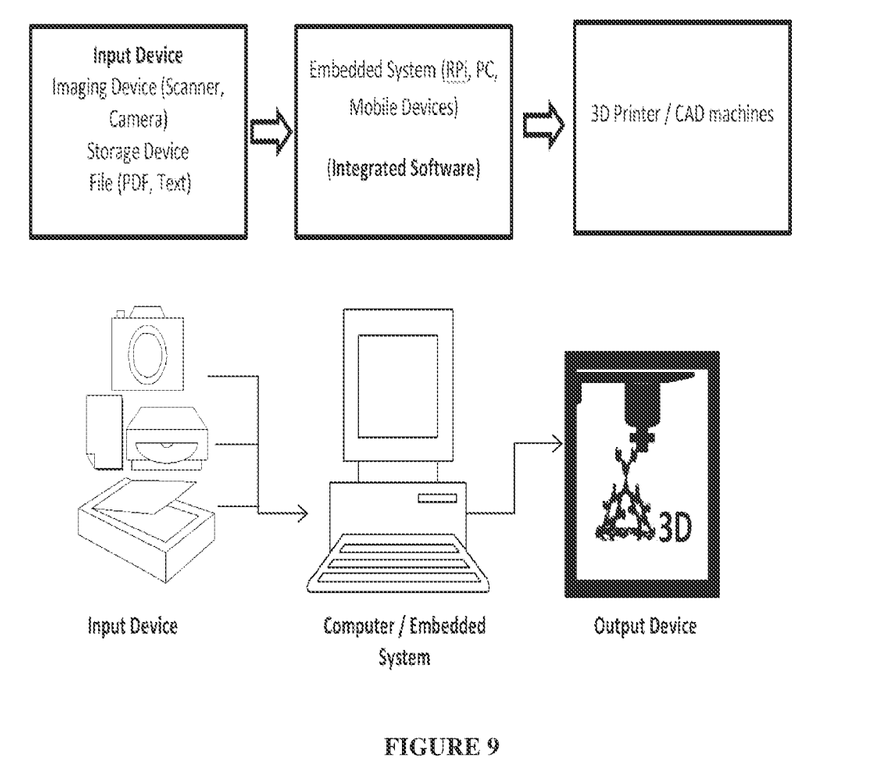
FIG. 9 illustrates the application of present method in embedded system

A comparative plot of single point energies of molecules extracted from coordinate data related Example 2 is illustrated in FIG. 8. The values are in agreement with the original computed data. CBS=Complete Basis set. RHF=restricted Hartre Fock.

Example 3

In order to handle several hundred PDF files to harvest truly computable molecular data that are buried in PDF files, the method can harvest atomic coordinate data mixed with images, for example spectral data, barcode images, experimental data, molecular description and other computed data. The molecules are processed and transformed into SDF format, which are compatible with commercial packages thus saving time and computational effort. Such step assists the readers to access the original input files even after passage of time. It is pertinent to mention here that the biological sciences and bioinformatics community follow a standard representation of molecular coordinates in the PDB file format which is a database compliant format instead of a PDF format thus securing an easy access and exchange of information. Extracting coordinates of protein molecule from a PDF file is a challenging task, assuming an average protein size of over 2,00,000 atoms. However with the aid of ChemEngine customized with additional atomic coordinate pattern recognition modules, now it is possible to harvest any molecular data from PDF format. With the advent of 3D structure repositories and several free academic sites, data storage is no longer a major issue, the ready to compute molecules can be deposited and maintained to avoid duplication of computational efforts.

Advantages of Invention

Easy extraction of data from pdf files
Conversion of data to reusable format
Employing the method of the present invention avoids unnecessary generation of molecular data and laborious recomputation of already published work

The invention claimed is:
1. A method for harvesting computable molecular data from a non-editable storage document and converting into recognizable data comprises
  feeding a non-editable storage document by a feeder;
  receiving the non-editable storage document by a receiver;
  recognizing and separating molecular and non-molecular data contained in the non-editable storage document by an analyzer;
  computing three-dimensional coordinates of said molecular data using a pattern recognition by the analyzer;
  encoding molecular coordinates by a pattern sequence by the analyzer, wherein the pattern sequence for encoding coordinates comprises two characters, followed by a space, an addition or subtraction symbol, a number, decimal and eight digits succeeding the decimal;
  generating cartesian coordinates bond matrix data from said encoded data by the analyzer;
  ensuring reusability of the data by the analyzer; and
  verifying the cartesian coordinates bond matrix data for accuracy by the analyzer with a stored standardized data into a library;

wherein the method enables large scale conversion of molecular information from supplementary data available in the non-editable storage document and avoids computational duplication.

2. The method according to claim 1, wherein recognizing and separating molecular and non-molecular data is executed by parsing method.

3. The method according to claim 1, wherein generation of cartesian coordinates bond matrix comprises computation of bond angles, bond lengths and dihedral angles, interatomic distances, sequence pattern of amino acids in proteins and the reusability of the data is ensured by calculation of single point energy.

4. The method according claim 1, wherein the conversion of data is output into a standard interoperability document.

5. A system harvesting for computable molecular data from a non-editable storage document and converting into recognizable data comprises:
   a feeder to feed a non-editable storage document,
   a receiver to receive a non-editable storage document,
   a library having standardized data stored,
   an analyzer wherein said analyzer
      recognizes and separates molecular and non-molecular data contained in said non-editable storage document,
      computes three-dimensional coordinates of the molecular data using a pattern recognition,
      encodes molecular coordinates by a pattern sequence, wherein said pattern sequence for encoding of coordinates by the analyzer comprises two characters, followed by a space, an addition or subtraction symbol, a number, decimal and eight digits succeeding the decimal,
      generates cartesian coordinates, bond matrix data from the encoded data,
      ensures reusability of the data,
      verifies the cartesian coordinates, bond matrix data for accuracy with a stored standardized data into a library.

6. The system according to claim 5, wherein the analyzer recognizes and separates molecular and non-molecular data by executing parsing method.

7. The system according to claim 5, wherein the analyzer generates cartesian coordinates bond matrix with computation of bond angles, bond lengths and dihedral angles, interatomic distances, sequence pattern of amino acids in proteins and further the analyzer ensures reusability of the data by calculation of single point energy.

8. The system according to claim 5, wherein the conversion of data is output into a standard interoperability document.

* * * * *